US010799128B2

(12) United States Patent
Paulussen et al.

(10) Patent No.: US 10,799,128 B2
(45) Date of Patent: Oct. 13, 2020

(54) OPTICAL VITAL SIGNS SENSOR

(71) Applicant: KONINKLIJKE PHILIPS N.V., Eindhoven (NL)

(72) Inventors: Elvira Johanna Maria Paulussen, Eindhoven (NL); Hugo Johan Cornelissen, Escharen (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 203 days.

(21) Appl. No.: 15/475,967

(22) Filed: Mar. 31, 2017

(65) Prior Publication Data

US 2017/0202466 A1 Jul. 20, 2017

Related U.S. Application Data

(63) Continuation of application No. PCT/EP2015/070911, filed on Sep. 14, 2015.

(30) Foreign Application Priority Data

Oct. 2, 2014 (EP) ..................................... 14187495

(51) Int. Cl.
  *A61B 5/024* (2006.01)
  *A61B 5/1455* (2006.01)
  *G01N 21/47* (2006.01)
  *G01N 21/49* (2006.01)

(52) U.S. Cl.
  CPC ...... *A61B 5/02427* (2013.01); *A61B 5/02438* (2013.01); *A61B 5/14552* (2013.01); *A61B 2562/0233* (2013.01); *A61B 2562/0238* (2013.01); *A61B 2562/0242* (2013.01); *G01N 21/4795* (2013.01); *G01N 21/49* (2013.01);
(Continued)

(58) Field of Classification Search
  None
  See application file for complete search history.

(56) References Cited

U.S. PATENT DOCUMENTS 5,299,570 A * 4/1994 Hatschek ........... A61B 5/14552
  356/41
6,002,829 A * 12/1999 Winston .................... F21V 5/02
  385/129
6,571,117 B1 5/2003 Marbach
(Continued)

FOREIGN PATENT DOCUMENTS

EP 0527703 A1 2/1993
EP 2229880 A1 9/2010
(Continued)

*Primary Examiner* — Carolyn A Pehlke
*Assistant Examiner* — Marjan Saboktakin

(57) ABSTRACT

An optical vital signs sensor configured to measure or determine vital signs of a user comprises a light source configured to generate a light beam having an angular range of angles of incidence. The light beam is directed towards the skin of the user. A photo detector is provided and is configured to detect light which is indicative of a reflection of the light beam from the light source in or from the skin of the user. The light source and the photo detector are arranged adjacent to each other and on the same side of the skin of the user. A light shaping unit is configured to shape the light beam of the light source before the light beam enters the skin by limiting the angular range of angle of incidence to less than 20°.

10 Claims, 18 Drawing Sheets

(52) U.S. Cl.
CPC .............. *G01N 2021/4752* (2013.01); *G01N 2021/4757* (2013.01)

(56) References Cited

U.S. PATENT DOCUMENTS

| | | |
|---|---|---|
| 6,745,061 B1 | 6/2004 | Hicks et al. |
| 8,005,624 B1 | 8/2011 | Starr |
| 2005/0218810 A1* | 10/2005 | Kwok ................... H01J 61/025 |
| | | 313/635 |
| 2006/0089546 A1 | 4/2006 | Mahony et al. |
| 2009/0024041 A1* | 1/2009 | Cho ..................... A61B 5/0059 |
| | | 600/476 |
| 2009/0033937 A1 | 2/2009 | Oh et al. |
| 2009/0054751 A1 | 2/2009 | Babashan et al. |
| 2010/0252721 A1 | 10/2010 | Xu |
| 2011/0087108 A1 | 4/2011 | Onoe et al. |
| 2011/0118574 A1 | 5/2011 | Chang et al. |
| 2012/0083673 A1* | 4/2012 | Al-Ali .................. A61B 5/0006 |
| | | 600/301 |
| 2013/0310668 A1 | 11/2013 | Young |
| 2013/0310669 A1 | 11/2013 | Nitzan |
| 2014/0064037 A1* | 3/2014 | Alameh ................ G04G 21/08 |
| | | 367/199 |

FOREIGN PATENT DOCUMENTS

| | | |
|---|---|---|
| JP | 2004290544 A | 10/2004 |
| RU | 99946 U1 | 12/2010 |
| WO | 9641566 A2 | 12/1996 |
| WO | 2007140210 A2 | 12/2007 |
| WO | 2009014419 A1 | 1/2009 |
| WO | 2009030934 A2 | 3/2009 |

\* cited by examiner

OPTICAL VITAL SIGNS SENSOR

CROSS REFERENCE TO RELATED APPLICATIONS

The present application is a continuation of International Application No. PCT/EP2015/070911, filed on Sep. 14, 2015, which claims the benefit of European Application No. 14187495, filed Oct. 2, 2014. These applications are hereby incorporated by reference herein for all purpose.

TECHNICAL FIELD

The embodiment relates to an optical vital signs sensor for monitoring vital signs of a user.

BACKGROUND

Optical heart rate sensors are well known to monitor or detect vital signs like a heart rate of a user. Such a heart rate sensor can be based on a photoplethysmograph (PPG) sensor and can be used to acquire a volumetric organ measurement. By means of pulse oximeters, changes in light absorption of a human skin is detected and based on these measurements a heart rate or other vital signs of a user can be determined. The PPG sensors comprise a light source like a light emitting diode (LED) which is emitting light into the skin of a user. The emitted light is scattered in the skin and is at least partially absorbed by the blood. Part of the light exits the skin and can be captured by a photodiode. The amount of light that is captured by the photo diode can be an indication of the blood volume inside the skin of a user. A PPG sensor can monitor the perfusion of blood in the dermis and subcutaneous tissue of the skin through an absorption measurement at a specific wave length. If the blood volume is changed due to the pulsating heart, the scattered light coming back from the skin of the user is also changing. Therefore, by monitoring the detected light signal by means of the photodiode, a pulse of a user in his skin and thus the heart rate can be determined.

FIG. 1 shows a basic representation of an operational principle of a heart rate sensor. In FIG. 1, a heart rate sensor is arranged on an arm of a user. The heart rate sensor 100 comprises a light source 110 and a photo detector 120. The light source 110 emits light onto or in the skin 1000 of a user. Some of the light is reflected and the reflected light can be detected by the photo detector 120.

U.S. 2009/033937 shows a sensor for measuring living body information having a light guide panel with a light extracting unit for outputting a first light towards the skin of a user and a light coupling pattern for guiding light from the skin towards a photo detector.

SUMMARY

It is an object of the embodiment to provide an optical vital signs sensor which is able to efficiently detect vital signs of a user while still having a reduced building height.

According to an aspect of the embodiment, an optical vital signs sensor is provided. The optical vital signs sensor is configured to measure or determine vital signs of a user. The optical vital signs sensor comprises a photoplethysmographic sensor PPG having a housing and a contact surface which is placed directly onto a skin of a user and at least one light source configured to generate a light beam having an angular range of an angle of incidence. The light beam is directed via the contact surface towards a skin of a user. Furthermore, at least one photo detector unit is configured to detect light which is indicative of a reflection of the light beam from the at least one light source in or from the skin of the user. The at least one light source and the at least one photo detector unit are arranged adjacent to each other inside the housing. A distance is present between the at least one light source and the at least one photo detector unit. The vital signs sensor furthermore comprises at least one light shaping unit arranged between the light source and the contact surface and is configured to shape the light beam from the at least one light source. This can be performed by limiting the angular range of the angle of incidence to less than 20°. The light shaping unit is a unit that is shaping, directing, controlling or managing the light beam to limit its angular range.

According to an aspect of the embodiment, the light shaping unit comprises an optical film which is able to reflect or redirect light beams having a large angle and to transmit light having a small angle of incidence.

According to a further aspect of the embodiment, the light shaping unit comprises a diffusion chamber which is configured to recycle light having a large angle of incidence.

According to a further aspect of the embodiment, the light shaping unit comprises a separating wall having a mirror side between the at least one light source and the at least one photo detector unit.

According to a further aspect of the embodiment, the light shaping unit comprises an optical refractive unit.

According to a further aspect of the embodiment, the light shaping unit comprises an optical collimation plate.

According to a further aspect of the embodiment, the at least one light source comprises a side emitting light emitting diode. The at least one light shaping unit comprises a light transport unit which is coupled with its first end to the at least one light source and wherein its distal end comprises an inclination such that light travelling through the light transport unit is reflected towards the skin of the user.

The embodiment also relates to a method of measuring or determining vital signs of a user. A contact surface of a housing of a PPG sensor is placed directly against a skin of a user. A light beam having an angular range of angles of incidence is generated by at least one light source in the PPG sensor. The light beam is directed via the contact surface towards the skin of the user and at least one photo detector unit in the housing is configured to detect light which is indicative of a reflection of the light beam from the at least one light source in or from the skin of a user.

A light shaping unit is arranged between the light source and the contact surface and is shaping the light from the light source to an angular range of less than 20°.

According to an aspect of the embodiment, a computer program product comprising a computer readable memory storing computer program code means for causing the optical vital signs sensor to carry out the steps of the method for measuring or determining vital signs of a user when the computer program is run on a computer controlling the optical vital signs sensor is provided.

According to an aspect of the embodiment, the vital signs sensor comprises a vital signs sensor which can be a LED based PPG sensor. The LED light penetrates the skin of the user and some of it can reach a photo detector. The output of the photo detector can be used to monitor a blood volume fraction and blood compounds like oxygenated and de-oxygenated hemoglobin. In particular, the amount of absorption or reflectance of the light from the LED light source can be used to determine the heart rate as well as the blood volume fraction or blood compounds. The heart rate relates to the blood volume fraction. Furthermore, the PPG sensor according to the embodiment is therefore an optical sensor allowing a non-invasive measurement of vital signs of a user.

It shall be understood that a preferred embodiment of the present embodiment can also be a combination of the dependent claims or above embodiments or aspects with respective independent claims.

These and other aspects of the embodiment will be apparent from and elucidated with reference to the embodiment(s) described hereinafter.

DETAILED DESCRIPTION OF EMBODIMENTS

Figure 1:
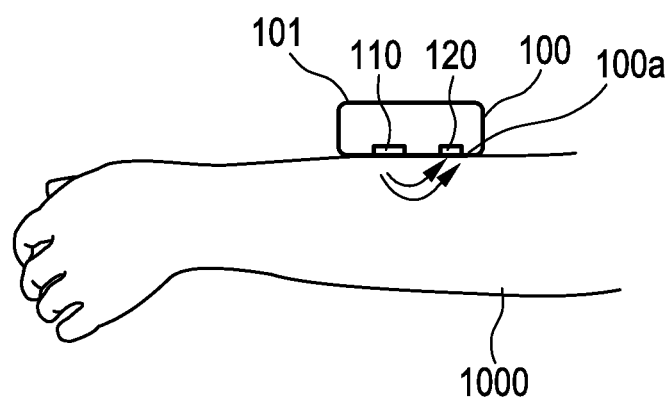
FIG. 1 shows a basic representation of an operational principle of a vital sign monitoring system.

According to an aspect of the embodiment, an optical vital signs sensor is provided which is based on a photoplethysmograph PPG sensor. Such a PPG sensor 100 is depicted in FIG. 1 and comprises a housing 101 with a contact surface 100a. A light source 110 emits light onto or into the skin 1000 of a user and some of the light is reflected and this reflected light can be detected by a photo detector 120. The output of the photo detector can be analyzed to determine a heart rate or other vital signs of a user. The contact surface 100a of the sensor 100 is placed in direct contact with the skin 1000 of the user.

The PPG sensor or optical vital signs sensor according to an aspect of the embodiment can be implemented as a wearable device or a wrist device (like a smart watch).

Figure 2:
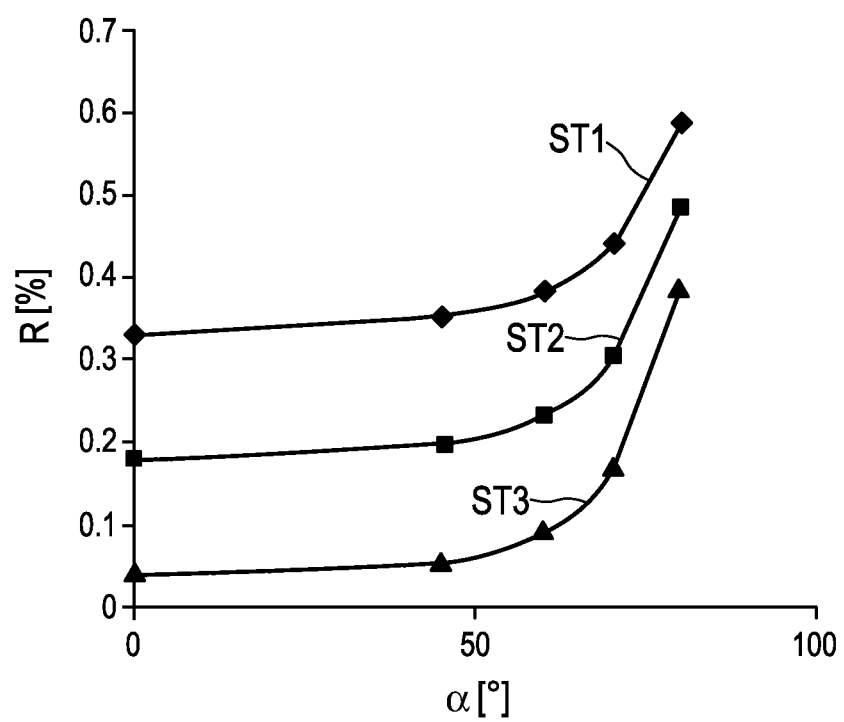
FIG. 2 shows a graph depicting simulated reflectance for different angles of incidences.

FIG. 2 shows a graph with a simulated reflectance on different skins of a user. In FIG. 2, the total reflectance R for different angles of incidences α are depicted for three different skin types. The simulation has been performed for a single wave length of 450 nm. In particular, three different skin types ST1-ST3 are depicted. The first skin type ST1 is a light skin with a melanin amount of 1.3%. The second skin type ST2 refers to a fair skin with a melanin amount of 4%. The third skin type ST3 refers to a dark skin with a melanin amount of 40%.

Figure 3:
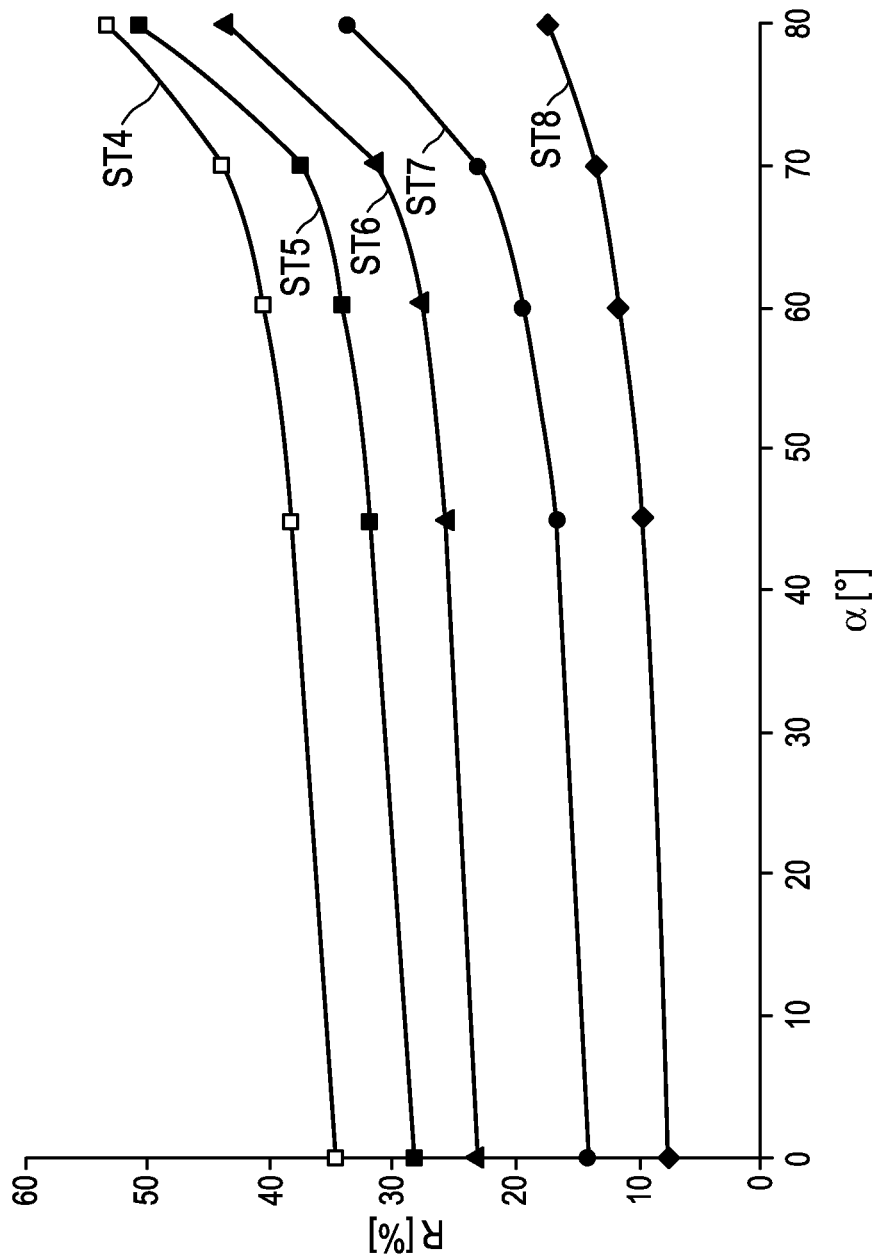
FIG. 3 shows a graph depicting measured reflectance for different angles of incidence and different skin types.

FIG. 3 shows a graph indicating measured reflectance as a function of different angles of incidences and different skin types. In FIG. 3, the total reflectance R in % is shown as a function of the angle of incidence α for five different skin types ST4-ST8. The skin types include the European light skin type ST4, an Asian skin type ST5, a south European skin type ST6, a European skin type (black hairy) ST7 and an African skin type ST8. The measurements of FIG. 3 have been performed at a center wave length of 450 nm. In FIG. 3, the measured reflectance as a function of angle of incidences is depicted for the different skin types, namely the skin type I to VI on the Fitzpatrick scale.

From FIG. 2 and FIG. 3, it can be seen that the reflectance significantly increases for high angles of incidences (for example >60°) as compared to a normal angle of incidence of 0°. The reason for this significant increase is due to Fresnel losses, i.e. reflectance losses on the skin surface.

Based on the simulated reflectance according to FIG. 2 as well as the measured reflectance according to FIG. 3, it becomes clear that about 20 to 30% of the light is reflected at a normal angle of incidence for the fair to white skin types, namely the skin types I-III. Furthermore, the specular component of the reflected light is high for larger angles of incidence like 70°. Accordingly, the diffuse reflectance is larger than the specular reflectance at all angles of incidence.

Figure 4:
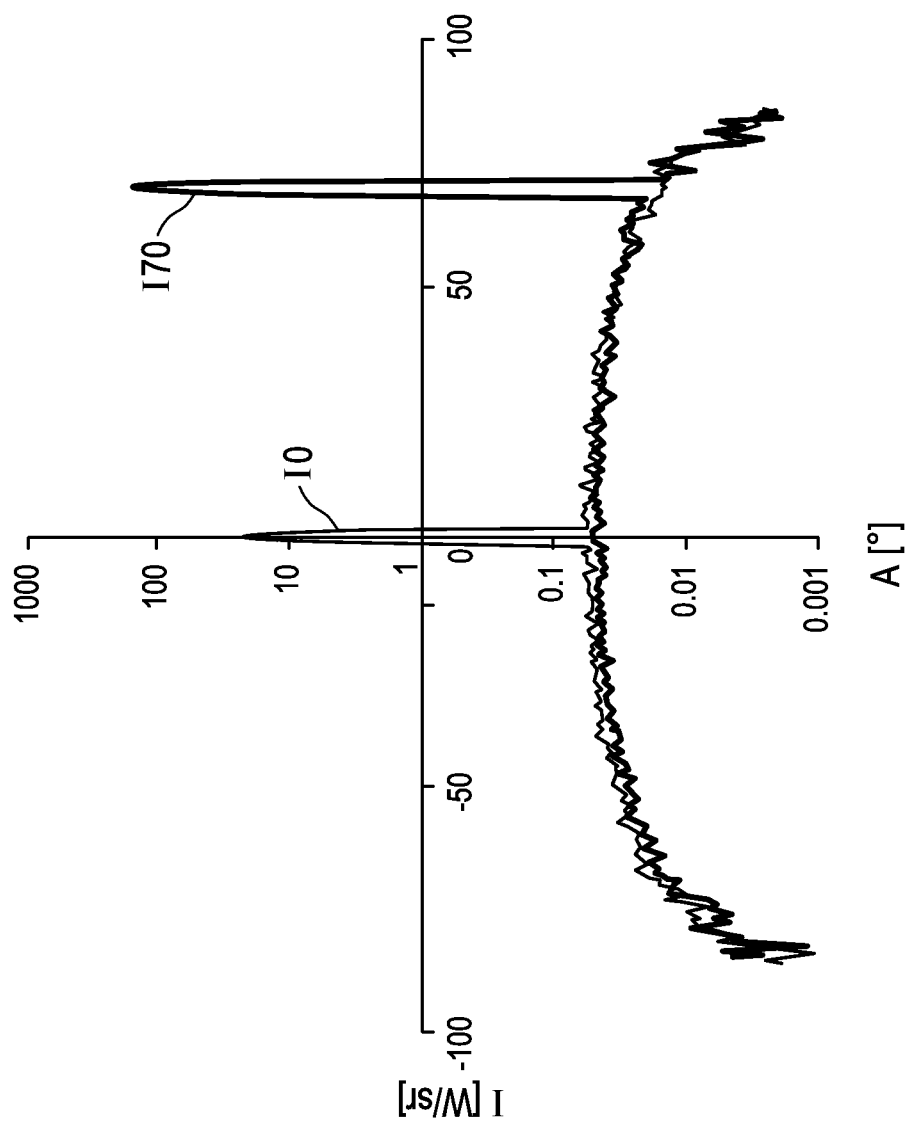
FIG. 4 shows a graph depicting light reflected from a skin of a user at two different angles of incidence.

FIG. 4 shows a graph depicting reflected light from a skin at two different angles of incidences. In particular, in FIG. 1, the angle A [°] and the intensity I of the reflected light is depicted. In FIG. 4, the reflected light I0 for an angle of incidence of 0° as well as the reflected light 170 for an angle of incidence of 70° is depicted.

Figure 5:
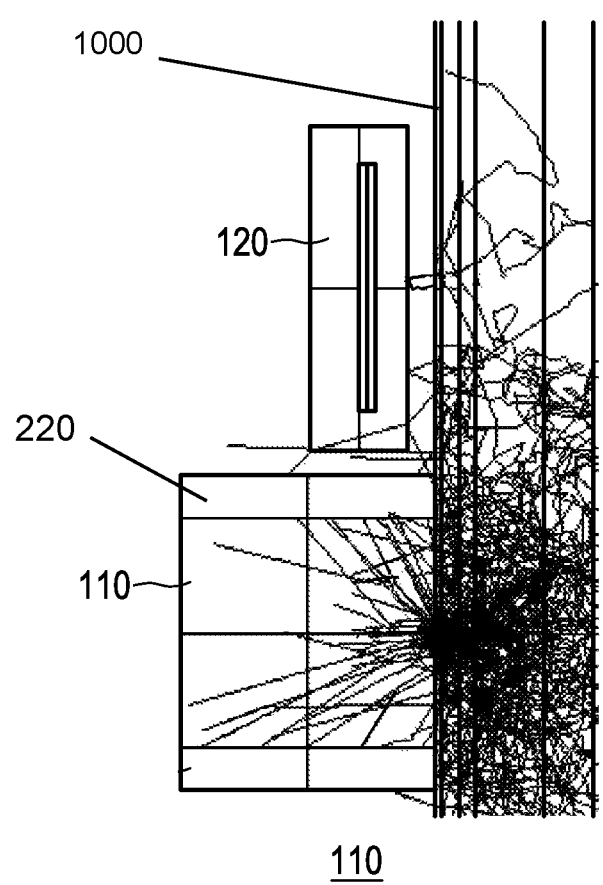
FIG. 5 shows a schematic cross section of a vital signs sensor according to an aspect of the embodiment.

FIG. 5 shows a schematic cross section of a vital signs sensor according to an aspect of the embodiment. The vital signs sensor comprises a light source 110, a photo detector 120 as well as a separation wall 220. Optionally, the separation wall can surround the light source. The separation wall 220 is used to separate the light source 110 from the photo detector 120. This can be done in order to avoid that light from the light source directly reaches the photodiode without any interaction with the skin 1000 of a user. FIG. 5 also shows some beam patterns to illustrate possible beam paths.

Figure 6:
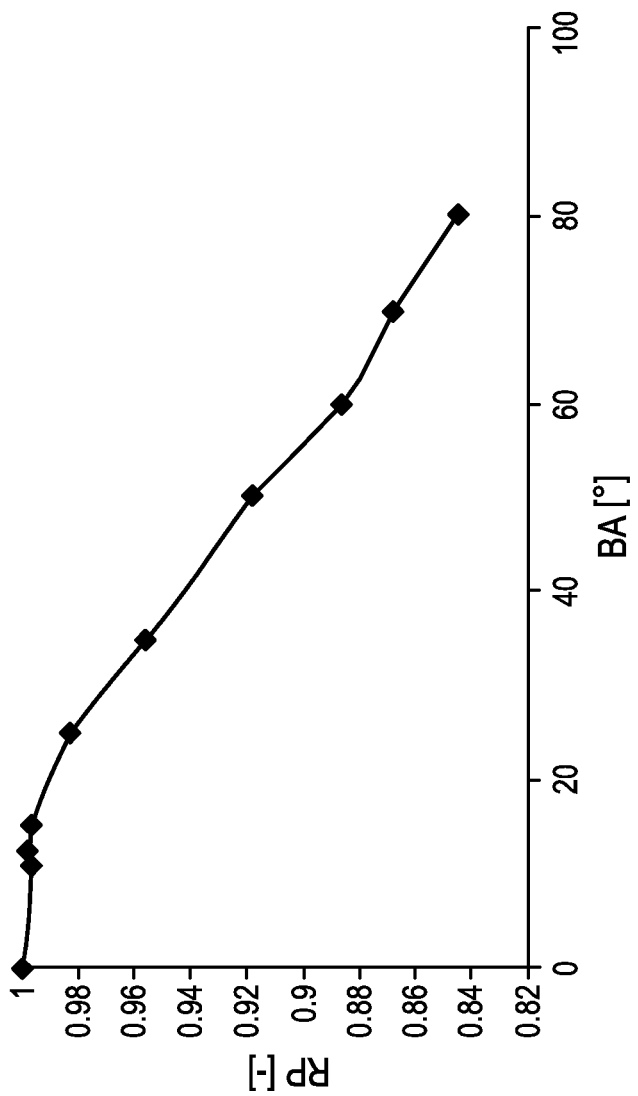
FIG. 6 shows a graph indicating the relation between the relative power on the photodiode and the beam angle.

FIG. 6 shows a graph indicating the relation of the relative power on the photodiode for different beam angles. In FIG. 6, the beam half angle BA as well as the relative power on the photodiode RP are depicted. As can be seen from FIG. 6, the power on the photodiode RP is decreasing with approximately 2% per 10° of the beam half angle (based on simulations for a Gaussian beam shape) if a half beam angle of 20° is considered. FIG. 4 shows the result of the reflected intensity per angle of incidence while FIG. 2 shows the reflectance per angle of incidence. As already mentioned above, because of Fresnel losses on the skin, the DC power of the photodiode will decrease with increasing beam angle.

Figure 7:
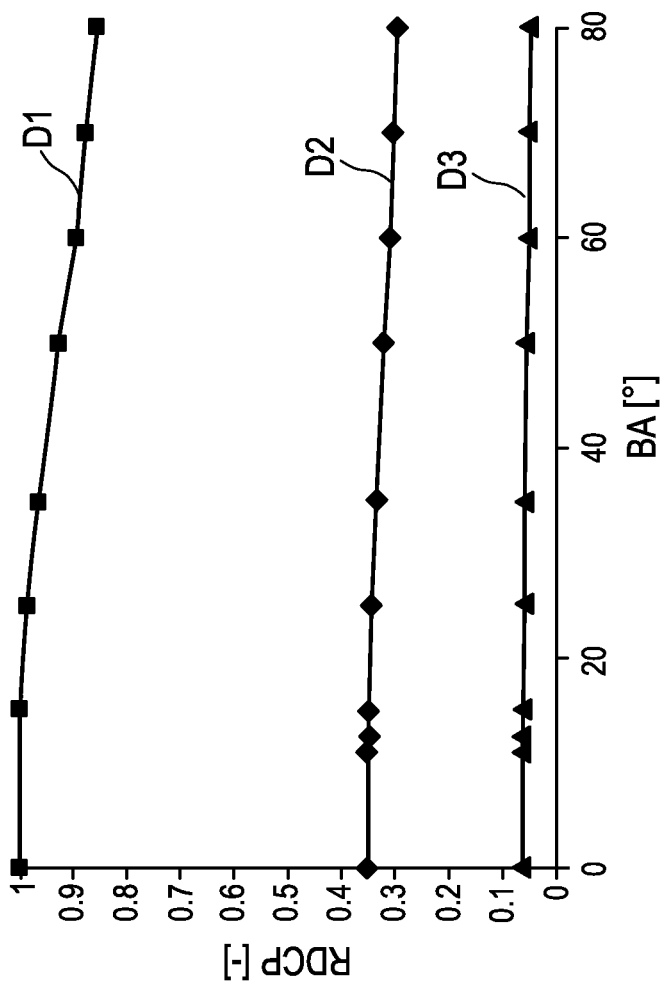
FIG. 7 shows a graph depicting the function of the relative DC power as a function of the beam angle at different distances of the light source.

FIG. 7 shows a graph indicating the relative DC power as a function of the beam half angle for different distances of the light source towards the skin. In particular, three distances D1-D3 are depicted, wherein the first distance D1 corresponds to 3.2 mm, the second distance D2 corresponds to 4.05 mm and the third distance D3 corresponds to 5.5 mm. As can be seen, the distance between the light source and the diode has a major influence on the relative DC power RDCP.

Figure 8B:
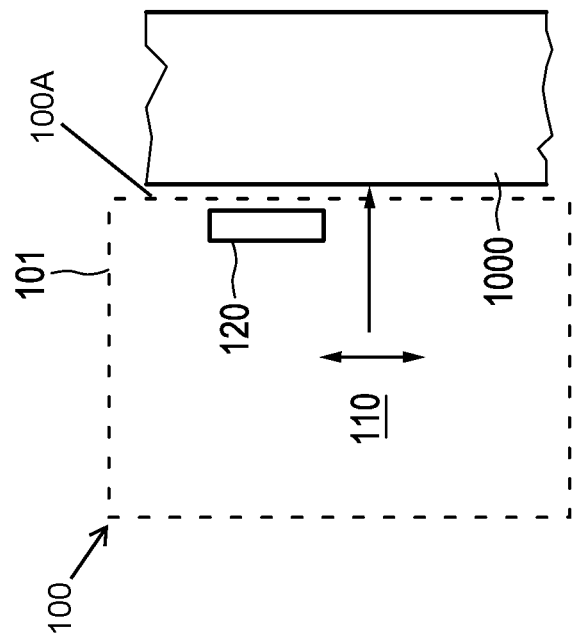
FIG. 8B shows a schematic representation of a vital signs sensor according to a further aspect of the embodiment.
Figure 8A:
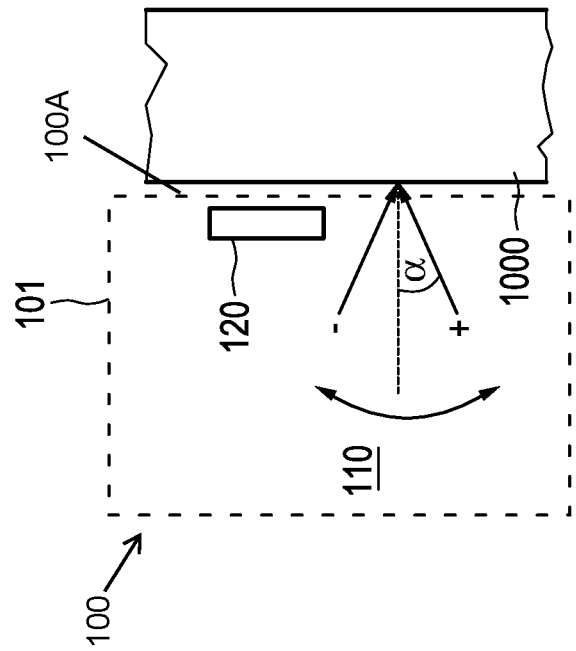
FIG. 8A shows a schematic representation of a vital signs sensor according to an aspect of the embodiment.

FIG. 8A shows a basic representation of a vital signs sensor according to an aspect of the embodiment. Here, the sensor 100 comprises a housing 101, a contact surface 100a as well as a light source 110 and a diode 120 inside the housing. The light from the light source 110 is directed towards the skin 1000 of the user and reflected light can be detected by the diode 120. According to this aspect of the embodiment, the distance between the light source 110 and diode 120 can be varied.

FIG. 8B shows a schematic representation of a vital signs sensor according to a further aspect of the embodiment. Here, the beam angle of incidence α of the light from the light source 110 is varied.

Figure 9:
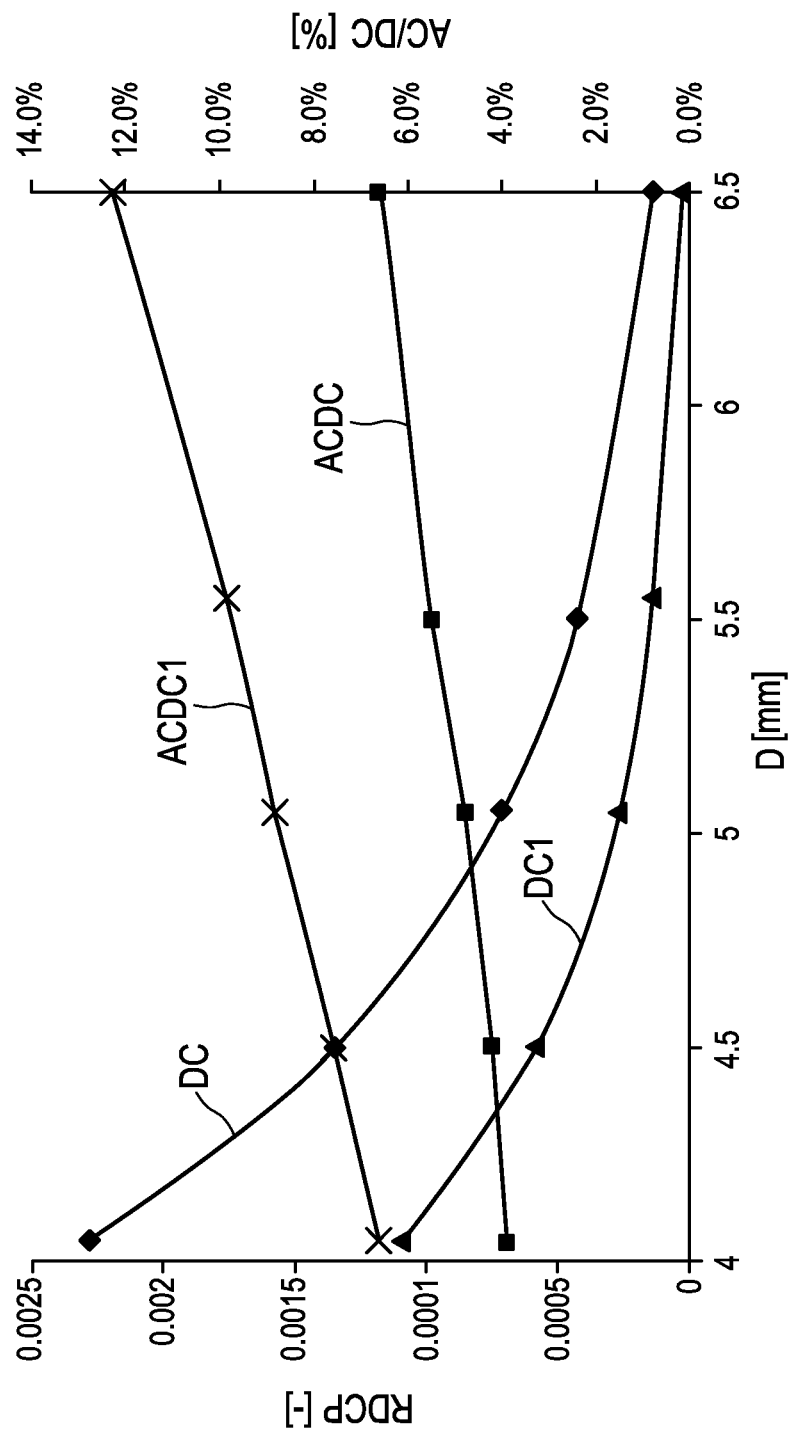
FIG. 9 shows a graph indicating the relative DC power and the AC/DC signal has a function of the light source distance.

FIG. 9 shows a graph indicating the relative DC power RDCP as function of the distance between the light source and the photodiode. Furthermore, the relation between the AC and DC power is also depicted as a function of the distance D between the light source and the diode.

Figure 10:
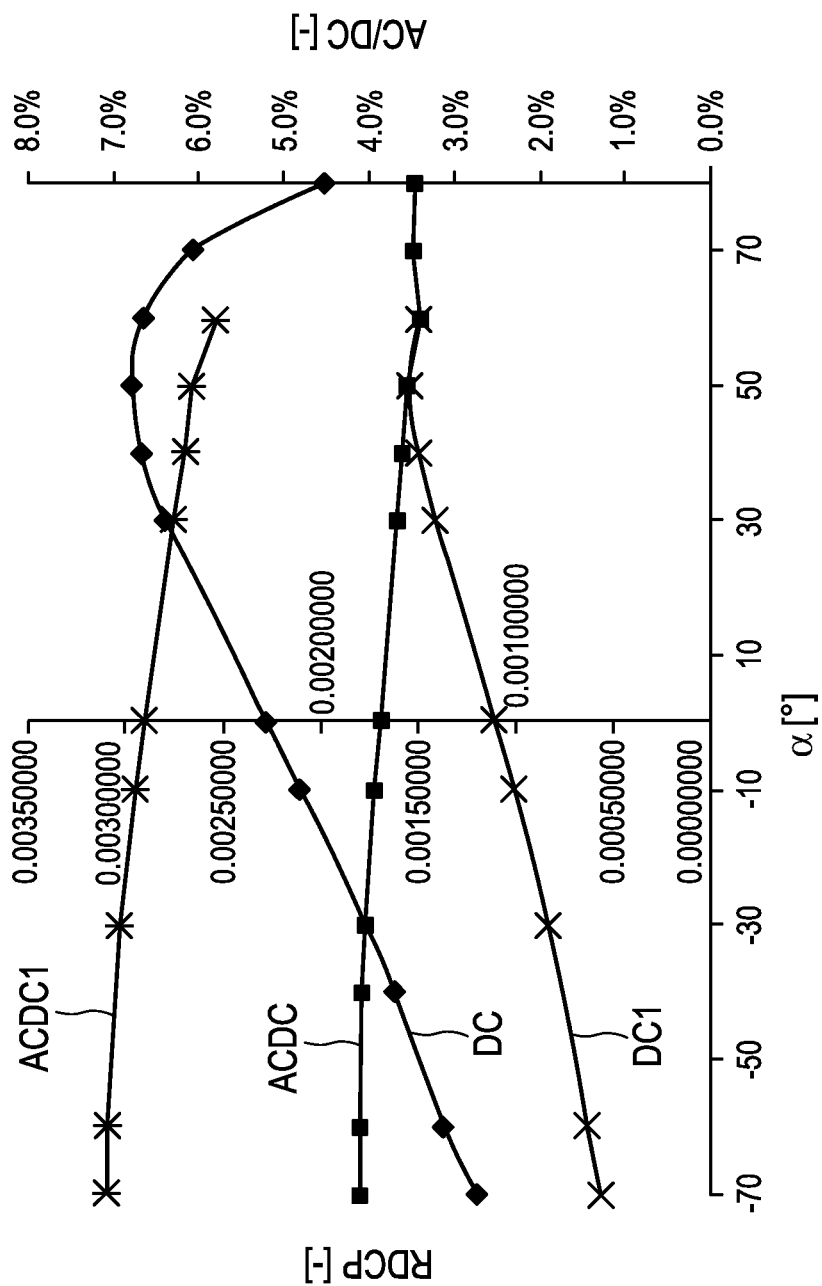
FIG. 10 shows a graph indicating the relative DC power and AC/DC signal as a function of angle of incidence.

FIG. 10 shows a graph indicating the relation between the relative DC power RDCP and the relation between AC and DC as a function of angle of incidence. FIG. 10 represents the results of the variation of the beam angle of incidence according to FIG. 8B.

In FIG. 9 as well as in FIG. 10, the relative DC power is shown for two different skin types and the AC/DC is shown for two different skin types.

Figure 11:
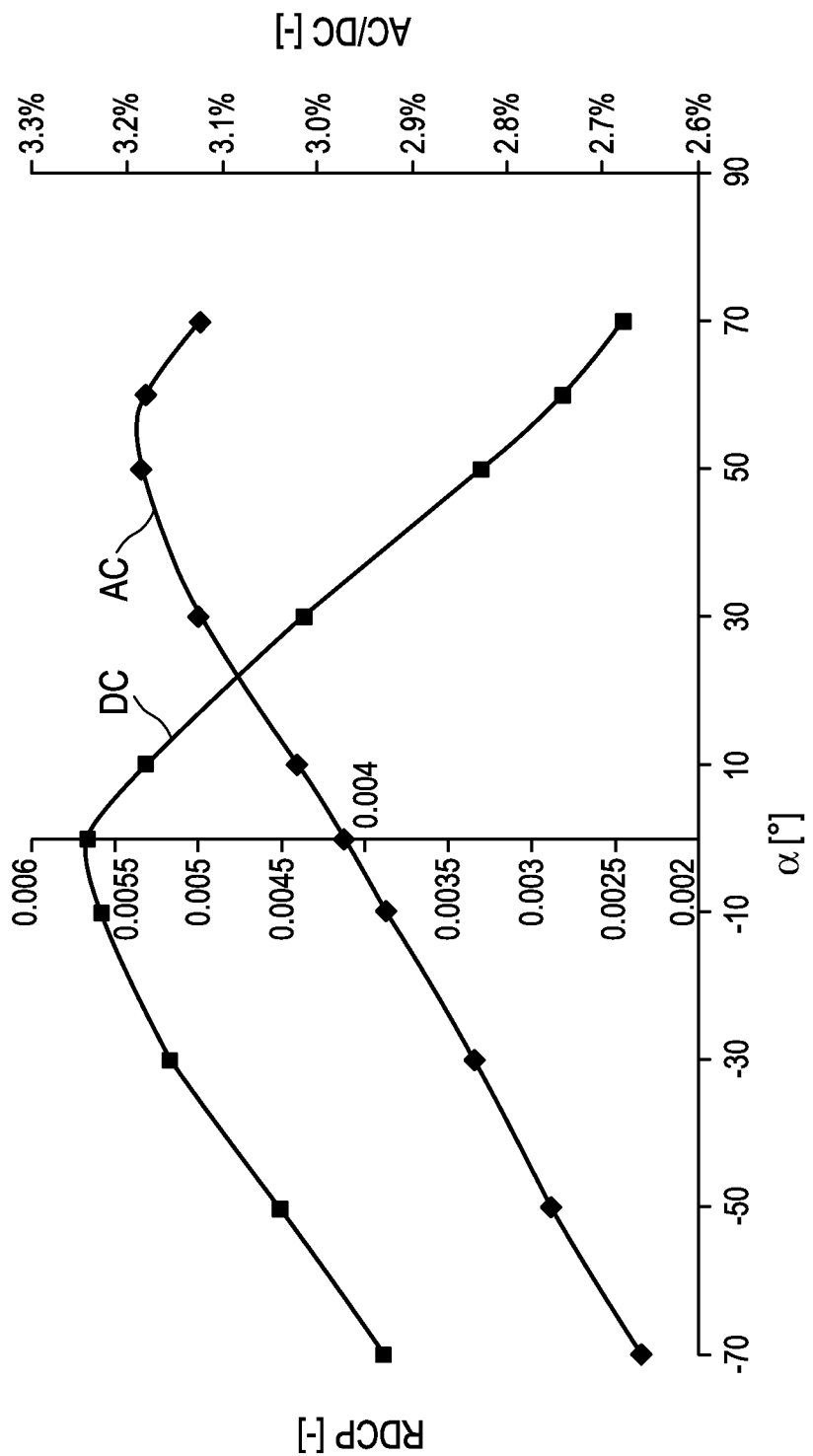
FIG. 11 shows a graph indicating a relative DC power and AC/DC signal as a function of the angle of incidence without a separation wall in the vital signals sensor according to an aspect of the embodiment.

FIG. 11 shows a graph indicating the relationship between the relative DC power and the AC/DC ratio versus the beam angle of incidence α. In particular, in FIG. 11, the situation is shown where the separation wall between the light source and the photodiode as shown in FIG. 5 is removed.

The difference between the graphs in FIGS. 10 and 11 is that in the situation of FIG. 10, a separation wall is present between the light source and the photo detector while in FIG. 11, the separation wall is missing. By the comparisons of the graphs of FIGS. 10 and 11, the effect on the beam angle on the AC/DC signal can be seen.

Figure 12:
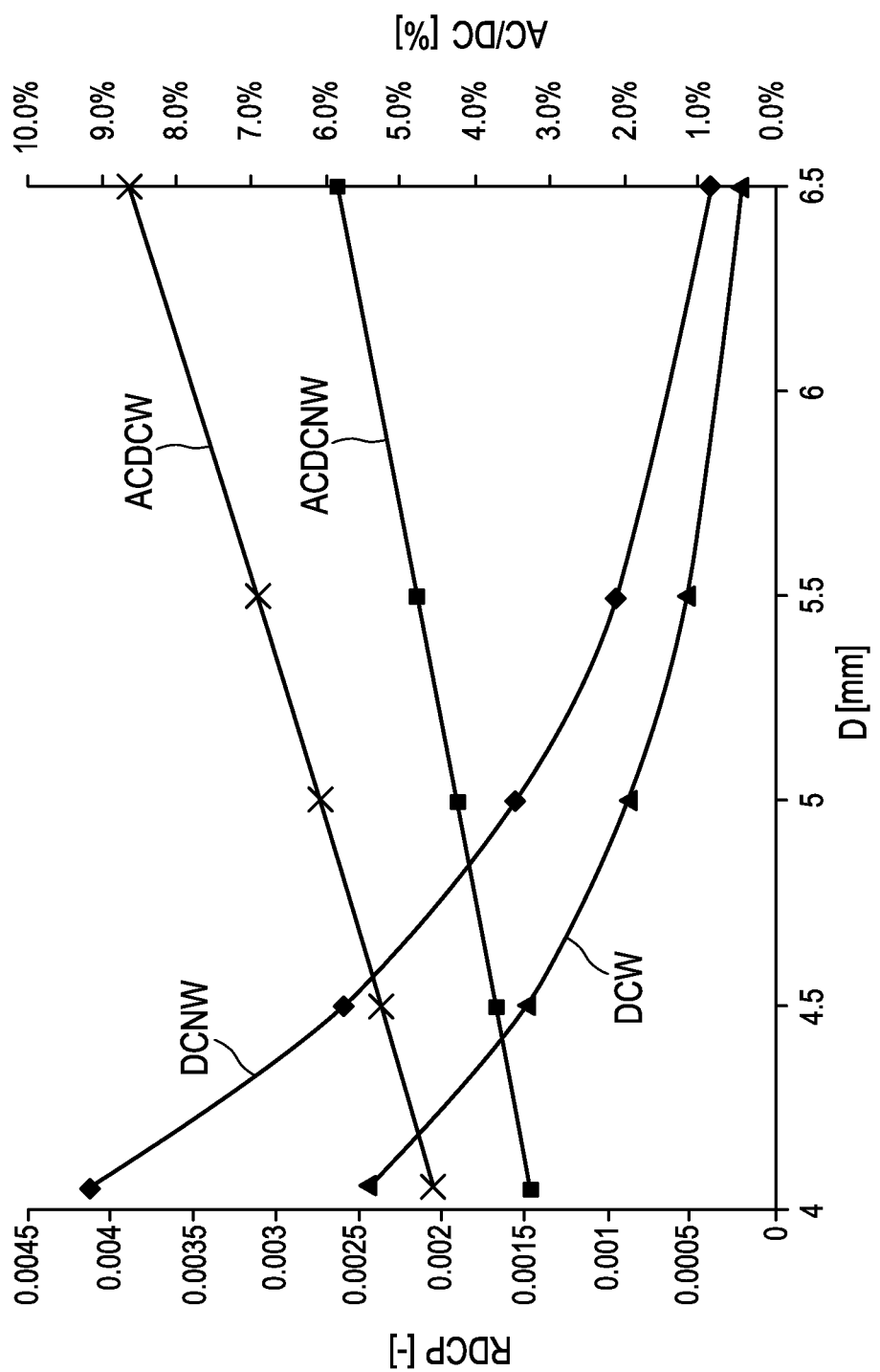
FIG. 12 shows a graph indicating the relative DC power and AC/DC signal as a function of the light source distance.

FIG. 12 shows a graph depicting the relative DC power and the DC/AC as a function of the distance between the light source and the diode. In particular, in FIG. 12, the DC signal DCW with a separation wall and the DC signal DCNW without a separation wall is depicted. Furthermore, the AC/DC signal with a wall ACDCW and the AC/DC signal ACDCNW without a wall is depicted.

Figure 13:
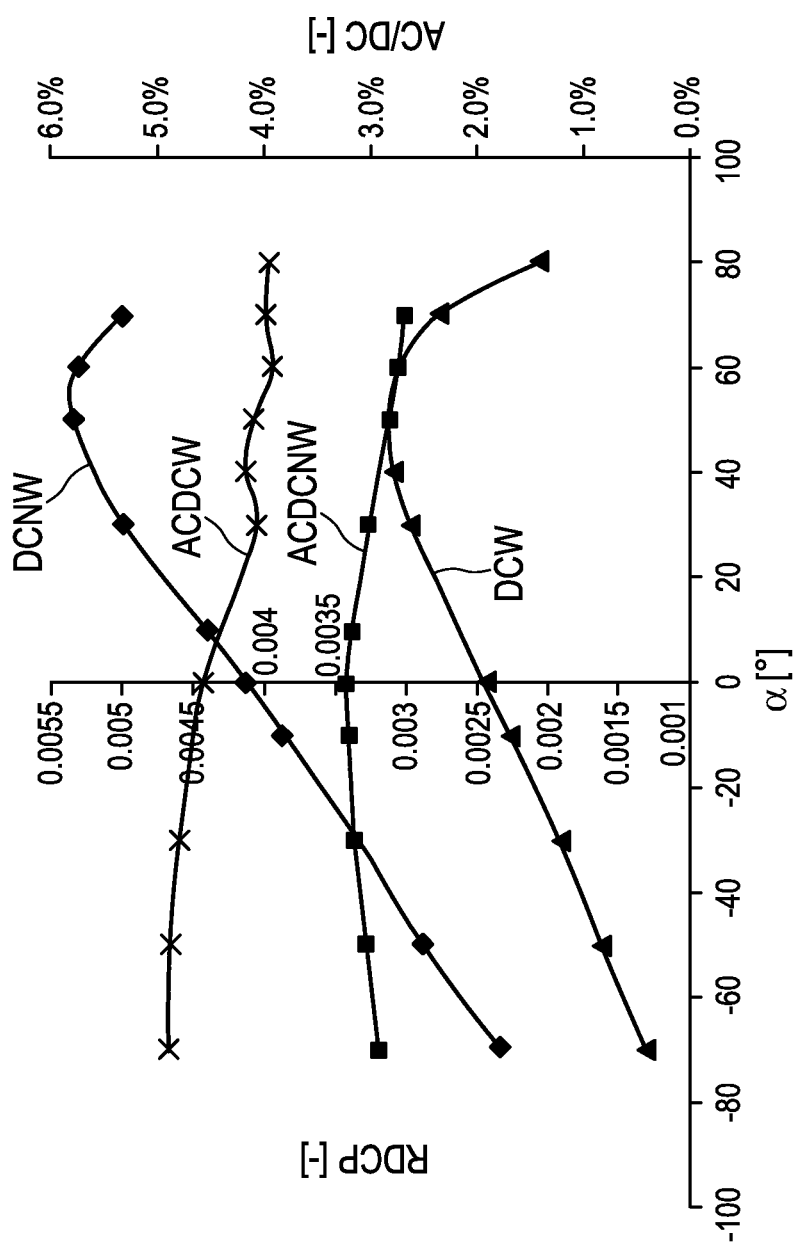
FIG. 13 shows a graph indicating a relative DC power and AC/DC signal as a function of angle of incidence with and without a separation wall in the vital signs sensor according to an aspect of the embodiment.

FIG. 13 shows a graph depicting the relative DC power and the AC/DC signal as a function of angle of incidence. In particular, in FIG. 13, the relative DC power is shown with and without a wall DCW, DCNW. The AC/DC signal is also shown with a wall and without a wall ACDCW, ACDCNW. For all cases in this graph, the distance between the light source and the photo diode is 4.05 mm.

According to the measurements as shown in the FIGS. 9 to 13, there is a relationship between the relative DC power and the AC/DC signal. One important property of the output signal is the modulation signal. The modulation signal relates to the ratio of the AC component to the DC component. The modulation AC/DC signal is important, because it is related to intrinsic properties of the skin. It covers the peek-to-peek value of the change in blood volume fraction in one heart pulse (AC signal), but also the skin-dependent reflectance (DC-component) which is important to know because a low reflectance can be compensated with LED power boost, preserving the same modulation signal.

In particular, the AC/DC signal decreases when the DC signal increases. If no separation wall is present between the light source and the photodiode, this relationship is valid for beam angles of >0°. Furthermore, if the distance between the light source and the diode increases, this also leads to an increase of the AC/DC signal. If the beam angle increases, the DC signal increases up to 50° and then starts to decrease for larger angles. This is probably due to the Fresnel losses on the skin surface. As can be seen from FIG. 13, beam angles of incidences above 45° and a small distance (e.g. less than 4 mm) between the light source and the photodiode should be avoided.

Furthermore, as can be seen in the Figs. above, in order to obtain an optimal AC/DC signal, the beam angle of incidence can be adapted.

Figure 14A:
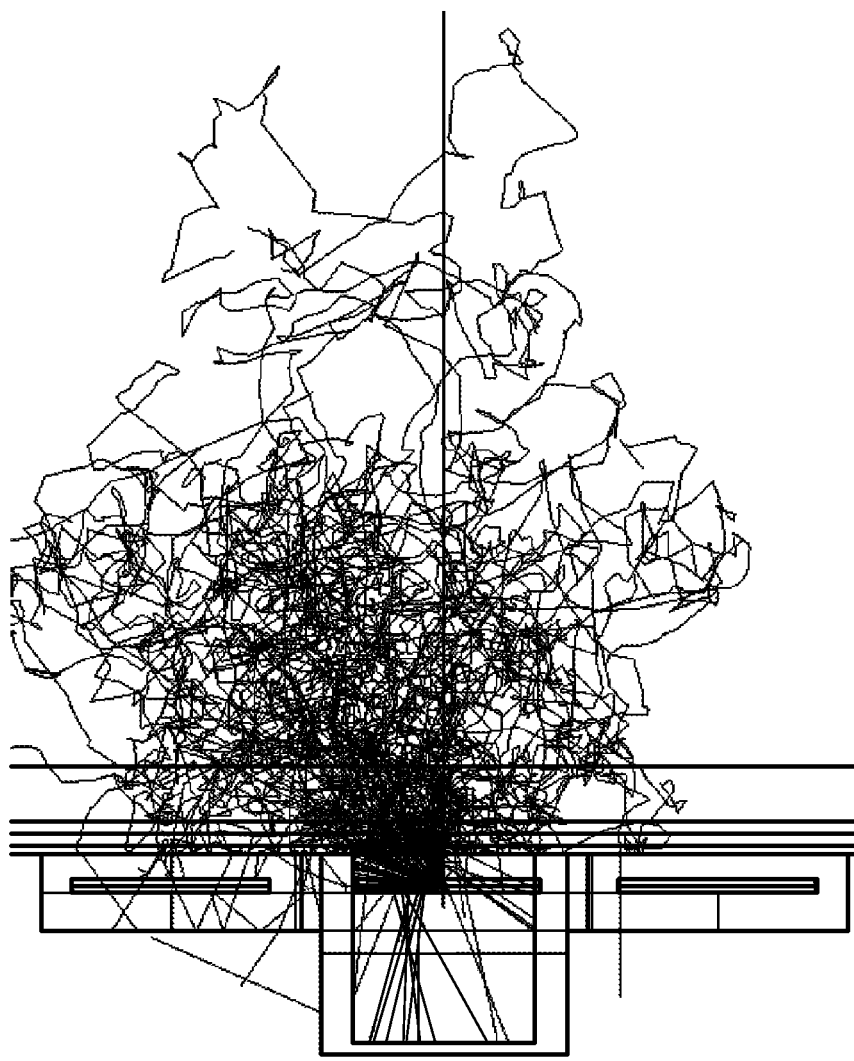
FIG. 14A shows a graph indicating a beam pattern in a vital signs sensor according to an aspect of the embodiment.
Figure 14B:
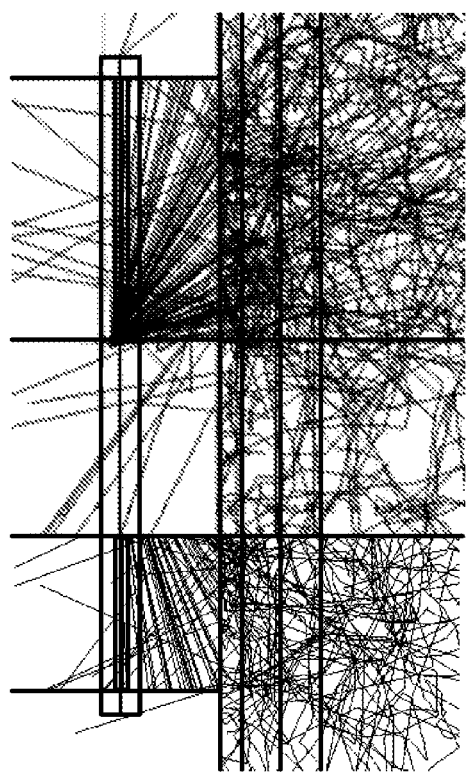
FIG. 14B shows a beam pattern in a vital signs sensor with angle of incidence with a negative direction.

FIGS. 14A and 14B show an angle of incidence of 45° in the positive direction and 45° in the negative direction. As seen from FIGS. 14A and 14B, two complete different modulation signals are obtained.

It should further be noted that the modulation signal, i.e. the AC/DC signal is sensitive towards the beam pattern and the angle of incidence. The greater the distance between the light source and the photodiode, the lower the sensitivity regarding the angle of incidence. Furthermore, according to an aspect of the embodiment, an angle of incidence of greater than 45° should be avoided while small beam angles around 0° and a beam angle pointing in the opposite direction as towards the photodiode can also be used. According to an aspect of the embodiment, an improved PPG signal can be obtained if the magnitude of the beam angle of the light source is less than 20°.

Figure 15:
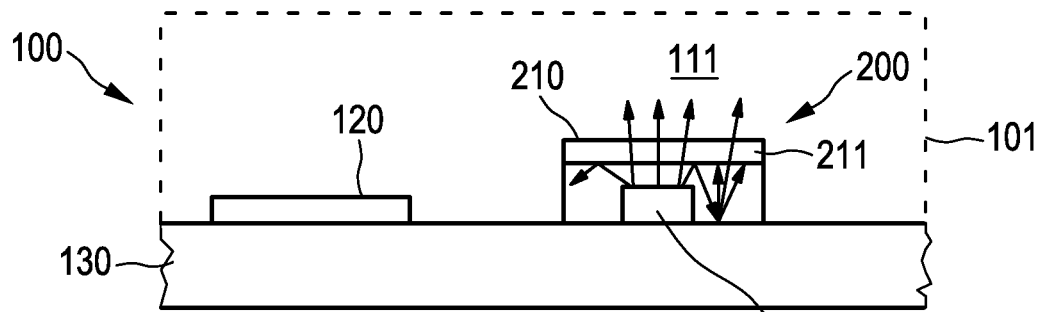
FIG. 15 shows a schematic representation of a vital signs sensor according to an aspect of the embodiment.

FIG. 15 shows a schematic representation of a vital signs sensor according to an aspect of the embodiment. The vital signs sensor 100 can be embodied as a PPG heart rate sensor and can comprise a housing 101, a contact surface 100a, at least one light source 110 and a photo detector 120. The light source 110 and the at least one photo detector 120 can be arranged on a mutual base material 130. The light source 110 can for example be embodied as a light emitting diode LED. Furthermore, the vital signs sensor comprises a light shaping means 200 which serves to guide, shape or direct or redirect the light 111 from the at least one light source 110. The light shaping unit 200 can also be used to shape a beam profile of the light 111 emitted by the at least one light source 110. In particular, the shaping unit is adapted to guide the light or light beam 111 such that it has angle of incidence of less than 20°. Advantageously, the range of the angle of incidence is between −20° and +20°. This will lead to an improved modulation signal, i.e. AC/DC signal.

In FIG. 15, the shaping unit 200 is implemented by a diffusing chamber 210 having a top plate 211 which is adapted to transmit light 111 from the at least one light source 110 if the light has a small angle of incidence while light with larger angles of incidences are reflected or redirected by the diffusing chamber. The top plate is the angle selective film or directional turning film (transmitting small angles and reflecting large angles). Thus, the diffusing chamber 210 only allows those light beams 111 to be transmitted or to pass through it if the angle of incidence is small. In fact, the diffusing chamber 210 can act as a mixing chamber and is used to recycle part of the light 111 from the at least one light source 110.

Figure 16:
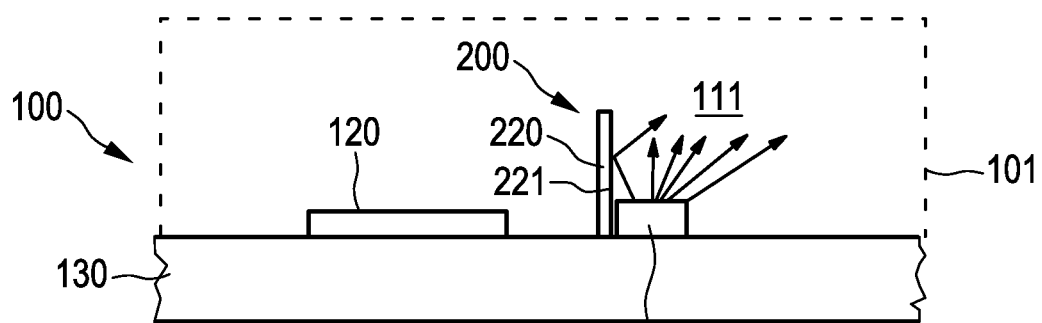
FIG. 16 shows a basic representation of a vital signs sensor according to an aspect of the embodiment.

FIG. 16 shows a basic representation of a vital signs sensor according to an aspect of the embodiment. The vital signs sensor according to FIG. 16 substantially corresponds to the vital signs sensor according to FIG. 15. Thus, the vital signs sensor also comprises a light shaping means 200. In the aspect of the embodiment according to FIG. 16, the light shaping means 200 is implemented as a separation wall 220 wherein the separation wall comprises a mirror side 221 which is the side towards the light unit 110. By means of the separation wall 220 which is arranged between the at least one photodiode 120 and the at least one light source 110, the light or light beam 111 from the light source is guided such that the light reaching the skin 1000 of the user has an angle of incidence between −60° and +20°, in particular between −20° and +20°. By means of the mirror side 221 of the separation wall 220, the light 111 is redirected such that it points towards the photodiode 120 in negative direction, i.e. it is pointing away from the photodiode 120.

Figure 17:
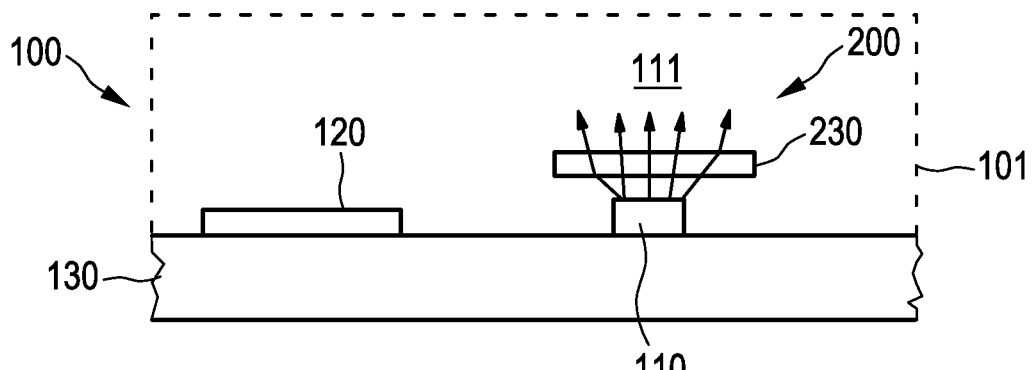
FIG. 17 shows a basic representation of a vital signs sensor according to a further aspect of the embodiment.

FIG. 17 shows a basic representation of a vital signs sensor according to a further aspect of the embodiment. The vital signs sensor according to the aspect of the embodiment according to FIG. 17 substantially corresponds to the vital signs sensor according to FIG. 15 or 16. Thus, the vital signs sensor 100 comprises at least one light source 110, at least one photo detector 120 and a light shaping unit 200 for guiding or shaping the light 111 from the at least one light source 110. Optionally, the at least one light source 110 and the at least one photo detector 120 can be arranged on a mutual base material 130. In the aspect according to FIG. 17, the light shaping unit 200 comprises an optical refractive unit 230. Such an optical refractive unit 230 can for example be a Fresnel lens. Here, any light 111 from the at least one light source 110 which has a large angle is refracted and can be redirected based on the property of the optical refractive unit 230. Thus, it can be ensured that the range of angle of incidences of the light 111 from the at least one light source which is entering the skin 1000 of the user is within a range of between −60° and +20°, in particular between −20° and +20°.

Figure 18:
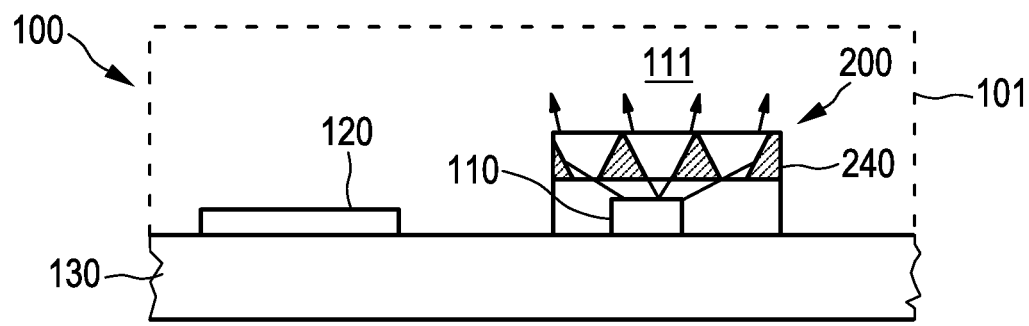
FIG. 18 shows a basic representation of a vital signs sensor according to a further aspect of the embodiment.

FIG. 18 shows a basic representation of a vital signs sensor according to a further aspect of the embodiment. The vital signs sensor according to the aspect of the embodiment of FIG. 18 substantially corresponds to the vital signs sensor according to FIG. 15, 16 or 17 and thus comprises at least one light source 110 and a photodiode 120. In addition, a light shaping unit 200 is provided for ensuring that the light which is entering the skin 1000 of a user has a specific range of angles of incidence, for example between −60° and +20°. According to the aspect of FIG. 18, this is achieved by a light shaping unit 200 which is implemented as an optical collimation plate. The optical collimation plate 240 is arranged in front of the at least one light source 111 and the light 111 from the at least one light source is reflected at the optical collimation plate 240 such that the angle of incidence of the light 111 which is entering the skin of the user is within a specific range of angle of incidence, namely between −60° and +20°.

Figure 19:
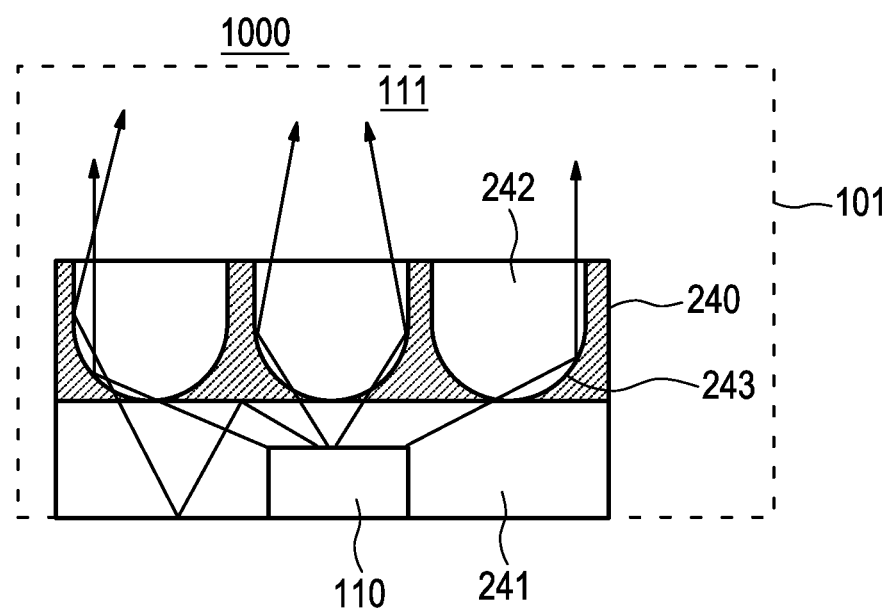
FIG. 19 shows a basic representation of a vital signs sensor according to a further aspect of the embodiment.

FIG. 19 shows a basic representation of a vital signs sensor according to a further aspect of the embodiment. The collimation plate 240 is used together with a mixing box 241. The collimation plate 240 comprises several recesses 242 which can be of compound parabolic concentrator-shape 243.

Figure 20:
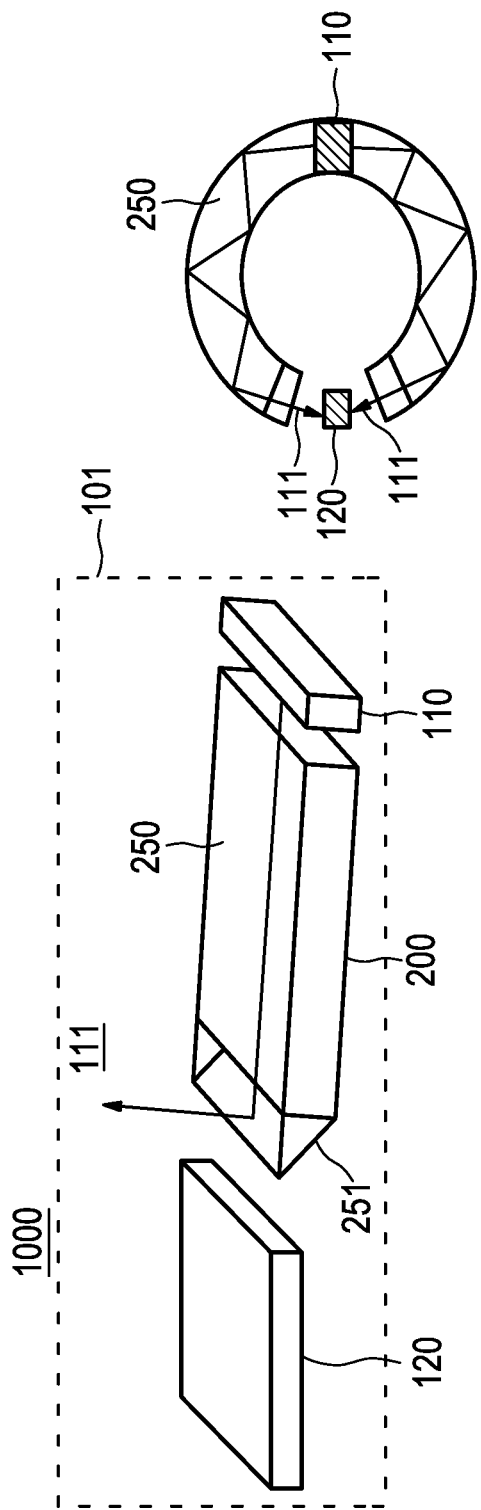
FIG. 20 shows a basic representation of a vital signs sensor according to a further aspect of the embodiment.

FIG. 20 shows a basic representation of a vital signs sensor according to a further aspect of the embodiment. The vital signs sensor according to an aspect of the embodiment according to FIG. 20 comprises at least one light source 110, at least one photodiode 120 as well as at least one light guide 200. According to this aspect of the embodiment, the light guide 200 is arranged between the at least one light source 110 and the at least one photodiode 120. The light guide 200 is implemented as a light transport unit 250 which is able to transport light from the at least one light source (for example a LED which is implemented as a side emitter) towards the at least one photodiode 120. The distal end of the light transport unit 250 has an inclination 251 such that the light 111 from the at least one light source 110 is redirected towards the skin of the user 1000. With such a light guide unit 200, the distance between the photodiode 120 and the output end of the light guide unit 250 can be significantly reduced and a flat design with a low building height is possible.

Figure 21:
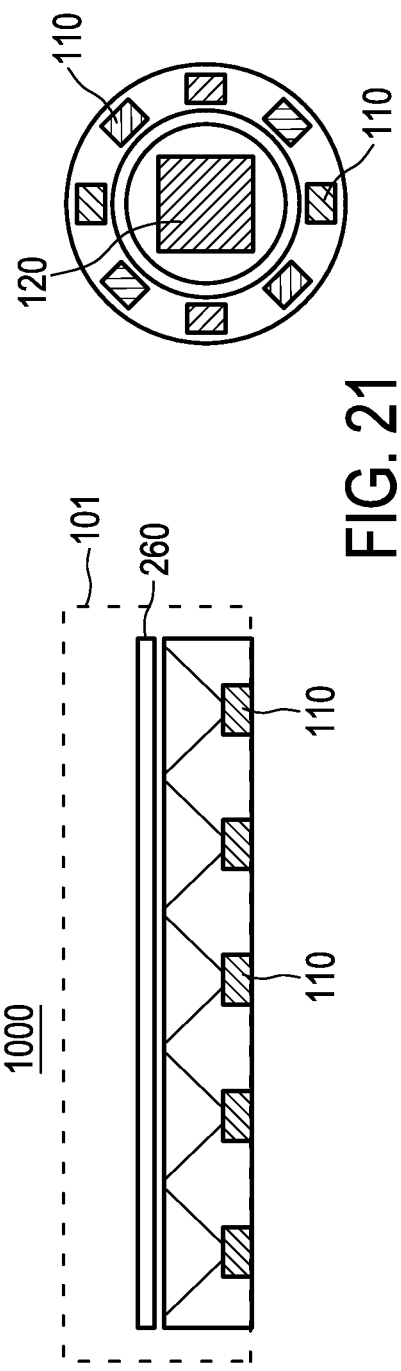
FIG. 21 shows a basic representation of a vital signs sensor according to a further aspect of the embodiment.

FIG. 21 shows a basic representation of a vital signs sensor according to a further aspect of the embodiment. The vital signs sensor can comprise at least one light unit 110, a photo detector 120 as well as a light shaping unit 200 which is arranged between the light source 110 and the skin 1000 of the user. The light shaping unit 200 can be implemented as an optical angle selective foil 260. The angle selective optical foil 260 is able to allow light to transmit within a selected angle range. Alternatively, the light guide unit can also be implemented with an optical holographic light shaping diffuser or direction turning film DTF.

The light shaping unit 200 is used to shape, direct, redirect, control or manage the light beam from the light source such that the angular range of the beam is limited or restricted. Thus the light shaping unit can be considered as a light directing or redirecting unit, a light control unit or a light management unit.

Other variations of the disclosed embodiment can be understood and effected by those skilled in the art in practicing the claimed embodiment from a study of the drawings, the disclosure and the appended claims.

In the claims, the word "comprising" does not exclude other elements or steps and in the indefinite article "a" or "an" does not exclude a plurality.

A single unit or device may fulfill the functions of several items recited in the claims. The mere fact that certain measures are recited in mutual different dependent claims does not indicate that a combination of these measurements cannot be used to advantage. A computer program may be stored/distributed on a suitable medium such as an optical storage medium or a solid state medium, supplied together with or as a part of other hardware, but may also be distributed in other forms such as via the internet or other wired or wireless telecommunication systems.

Any reference signs in the claims should not be construed as limiting the scope.

The invention claimed is:

1. An optical vital signs sensor comprising a photoplethysmographic sensor having:
   a first curved light guide having a first contact surface and a first inclined distal end;
   a second curved light guide having a second contact surface and a second inclined distal end that is separated by a space from the first inclined distal end, wherein the first contact surface and second contact surface are configured to be placed directly onto a skin of a user;
   at least one light source configured to generate light beams,
      wherein the first curved light guide receives a portion of the light beams from a side of the at least one light source and is arranged to transport the portion of light beams to the skin of the user via the first inclined distal end of the first curved light guide, and
      wherein the second curved light guide receives another portion of the light beams from a different side of the at least one light source and is arranged to transport the other portion of light beams to the skin of the user via the second inclined distal end of the second curved light guide; and
   at least one photodiode configured to detect light reflected from the skin of the user,
      wherein the at least one photodiode is arranged in the space between the first inclined distal end and the second inclined distal end to detect light that is being supplied by the at least one light source, transported via the first curved light guide and the second curved light guide, and reflected from the skin of the user.

2. The optical vital signs sensor according to claim 1, wherein the optical vital signs sensor is a wearable device or a wrist device.

3. The optical vital signs sensor of claim 1, wherein the first contact surface and the second contact surface are co-planar.

4. The optical vital signs sensor according to claim 1, wherein the first curved light guide, the second curved light guide, the at least one light source, and the at least one photodiode are contained in a common housing.

5. The optical vital signs sensor according to claim 1, wherein the angular range of an angle of incidence with respect to the first contact surface and second contact surface is limited to an angular range of less than 20°.

6. An optical vital signs sensor comprising a photoplethysmographic sensor having:
   a housing with a contact surface configured to be placed directly onto a skin of a user;
   at least one light source configured to generate a light beam, wherein at least some of said light beam is emitted through the contact surface and is directed towards the skin of the user;
   at least one photo detector unit configured to detect light which is indicative of a reflection of the light beam from the at least one light source in or from the skin of the user, wherein the at least one light source and the at least one photo detector unit are arranged adjacent to each other inside the housing with a distance between them; and
   a diffusion chamber arranged between the at least one light source and the contact surface and configured to shape the light beam of the at least one light source such that a portion of the light beam having angles of incidence ($\alpha$) with respect to the contact surface of less than 20° is permitted to pass through the contact surface, and any portion of the light beam having angles of incidence ($\alpha$) with respect to the contact surface that are greater than 20° are prevented from passing through the contact surface;
      wherein the diffusion chamber is configured to recycle light beams from the at least one light source and includes a top plate that: is suspended above the at least one light source, is connected to a surface of the housing by two side walls, and includes an angle selective file or a directional turning film, and
      wherein the at least one light source is disposed onto the surface of the housing between the two side walls.

7. The optical vital signs sensor according to claim 6, wherein the optical vital signs sensor is a wearable device or a wrist device.

8. An optical vital signs sensor comprising a photoplethysmographic sensor having:
   a housing comprising a contact surface that is configured to be placed directly onto a skin of a user and a planar surface that is parallel to and opposing the contact surface;
   at least one light source disposed onto the planar surface and configured to generate a light beam, wherein at least some of said light beam is emitted through the contact surface and is directed towards the skin of the user;
   at least one photo detector unit disposed onto the planar surface of the housing and configured to detect light which is indicative of a reflection of the light beam in or from the skin of the user, wherein the at least one light source and the at least one photo detector unit are arranged adjacent to each other inside the housing with a distance between them; and
   a separation wall arranged on the planar surface between the at least one light source and the contact surface and configured to shape the light beam of the at least one light source such that a portion of the light beam, having angles of incidence ($\alpha$) with respect to the contact surface of less than 20°, is permitted to pass through the contact surface, and any other portion of the light beam, having angles of incidence ($\alpha$) with respect to the contact surface that are greater than 20°, are prevented from passing through the contact surface;
      wherein the separation wall extends perpendicular to the contact surface and the planar surface, and the separation wall comprises a mirror side that faces the at least one light source.

9. The optical vital signs sensor according to claim 8, wherein the light beam, upon coming in contact with the mirror side of the contact surface, is re-directed away from the at least one photo detector unit.

10. The optical vital signs sensor according to claim 8, wherein the optical vital signs sensor is a wearable device or a wrist device.

* * * * *